United States Patent [19]

Siegmund et al.

[11] Patent Number: 5,711,915
[45] Date of Patent: Jan. 27, 1998

[54] OPTICAL SOLID-PHASE BIOSENSOR BASED ON POLYIONIC LAYERS LABELLED WITH FLUORESCENT DYES

[75] Inventors: Hans-Ulrich Siegmund, Krefeld; Ludger Heiliger, Leverkusen; Boudewijn van Lent, Bergisch Gladbach; Arno Becker, Krefeld, all of Germany

[73] Assignee: Bayer Aktiengesellschaft, Leverkusen, Germany

[21] Appl. No.: 547,272

[22] Filed: Oct. 24, 1995

Related U.S. Application Data

[63] Continuation of Ser. No. 28,858, Mar. 10, 1993, abandoned.

[30] Foreign Application Priority Data

Mar. 18, 1992 [DE] Germany ............ 42 08 645.0

[51] Int. Cl.$^6$ ............ C12M 1/40; C12Q 1/68; C07H 21/02; C07H 21/04
[52] U.S. Cl. ............ 422/68.1; 422/50; 422/55; 422/56; 422/57; 422/69; 422/82.05; 422/82.06; 422/82.07; 422/82.08; 435/6; 435/7.1; 435/7.92; 435/174; 435/180; 435/181; 435/283.1; 435/287.1; 435/287.2; 435/287.3; 435/287.7; 435/287.8; 435/287.9; 435/288.7; 435/290.1; 435/292.1; 435/808; 436/501; 436/518; 436/524; 436/527; 436/528; 436/531; 436/532; 436/535; 436/63; 436/164; 436/169; 436/170; 935/76; 935/77; 935/78; 935/85; 935/86
[58] Field of Search ............ 435/6, 7.1, 7.92, 435/174, 180, 181, 283.1, 287.1, 287.2, 287.3, 287.7, 287.8, 287.9, 288.7, 290.1, 292.1, 808; 422/50, 55, 56, 57, 68.1, 69, 82.05, 82.06, 82.07, 82.08; 436/501, 518, 524, 527, 528, 531, 532, 535, 63, 164, 169, 170; 935/76–78, 85, 86

[56] References Cited

U.S. PATENT DOCUMENTS

| 5,194,393 | 3/1993 | Hugl et al. .................... 436/525 |
| 5,208,111 | 5/1993 | Decher et al. .................... 428/420 |

FOREIGN PATENT DOCUMENTS

| 0150905 | 8/1985 | European Pat. Off. . |
| 0410323 | 1/1991 | European Pat. Off. . |
| 0429907 | 6/1991 | European Pat. Off. . |
| 0447133 | 9/1991 | European Pat. Off. . |
| 0472990 | 3/1992 | European Pat. Off. . |
| 3938598 | 5/1991 | Germany . |
| 4026978 | 2/1992 | Germany . |
| 4114482 | 11/1992 | Germany . |
| 4116116 | 11/1992 | Germany . |

OTHER PUBLICATIONS

Barnard, et al., "Chemical Sensors Based on Controlled-Release Polymer Systems", *Science*, vol. 251, No. 4996, Feb. 25, 1991, pp. 927–929.

Ullman, et al., "Fluorescence Excitation Transfer Immunoassay (FETI)", *Methods In Enzymology, Immunochemical Techniques*, vol. 74, Part C, 1981, pp. 28–60.

(List continued on next page.)

*Primary Examiner*—Ardin H. Marschel
*Attorney, Agent, or Firm*—Sprung Kramer Schaefer & Briscoe

[57] ABSTRACT

The present invention relates to an optical solid-phase biosensor for the detection of molecules which can be labelled with a fluorescent dye for the identification of substances in solution, for which there exists a biomolecule (receptor) which specifically recognises these and is chemically bonded to the uppermost layer of one or more layers of polyions on the surface of the sensor, by measurement of the Förster transfer between another dye molecule which is bonded in one of the uppermost layers of the sensor, and the said dye molecule.

8 Claims, 1 Drawing Sheet

OTHER PUBLICATIONS

Pachmann, et al., "Poly–L–lysine as a coating agent . . . ", *Biomedicine*, vol. 33, No. 7, 1980, pp. 210–211.

Japanese Abstract Publication No. JP 1126557 (1989).

Japanese Abstract Publication No. JP 2168162 (1990).

E.F. Ulman, P.L. Khanna, Methods in Enzymology, 74 (1981), pp. 28–60.

L. Stryer, Annual Reviews in Biochemistry 47 (1978), pp. 819–846.

S.M. Barnard, D.R. Walt, Science 251, 927–929.

R.G. Sommer et al., Clin. Chem. 36, pp. 201–206 (1990).

Patel et al. (1983) Analytical Biochemistry, vol. 129, pp. 162–169.

OPTICAL SOLID-PHASE BIOSENSOR BASED ON POLYIONIC LAYERS LABELLED WITH FLUORESCENT DYES

This application is a continuation of application Ser. No. 08/028,858, filed Mar. 10, 1993 now abandoned.

BACKGROUND OF THE INVENTION

1. Field of the Invention

The present invention relates to an optical biosensor for the detection of molecules which can be labelled with a fluorescent dye, for the identification of dissolved substances (called analytes hereinafter), for which there exists a biomolecule (called receptor hereinafter) which specifically recognises these. This takes the form of a solid-phase sensor with fluorescent dye which permits via an energy transfer process to a molecule which is to be detected, and which is labelled with a second fluorescent dye, the determination of its presence and amount. The determination of unlabelled analytes is also possible via a displacement reaction or a sandwich reaction.

2. Description of the Related Art

There are various methods for the detection of analytes such as hormones, enzymes, other proteins, carbohydrates, nucleic acids, pharmacological active substances, toxins and others in liquid samples of biological origin. Outstanding among the known methods are, in particular, immunoassays and methods related thereto, as a sensitive detection method for the determination of very small amounts of organic substances. Immunoassay methods are generally based on the ability of a receptor molecule, for example of an antibody, to recognise specifically the structure and molecular organisation of a ligand molecule, whether it is defined by non-polar and/or polar interactions, and to bind this molecule quite specifically in such a way.

Immunoassays are carried out by various methods. These include the use of different labelling techniques, usually radioactive, enzyme-coupled and fluorescent in nature (E. F. Ulman, P. L. Khanna, Methods in Enzymology, 74 (1981), 28–60). Radiationless fluorescence energy transfer can be considered as a special case of the last-mentioned method and can be used to measure the approach together of two fluorescent dyes and, via this, indirectly the approach together of a receptor/ligand pair (L. Stryer, Annual Reviews in Biochemistry 47 (1978), 819–846). This principle has been mentioned several times in the technology of immunoassays and biosensors (S. M. Barnard, D. R. Walt, Science 251, 927 (1991); EP 150 905; DE 3938598).

It is particularly advantageous to use an excess of donor dye to acceptor dye (DE 3938598). However, for this the former must be applied homogeneously in a layer which, corresponding to the Förster radius, is less than 5 to 10 nm thick, and is preferably monomolecular, on a solid support material. This has been achievable in the state of the art to date by means of the Langmuir-Blodgett technique or by chemisorption. Both methods either require elaborate apparatus, are subject to certain limitations concerning the shape of the substrates to be coated, or require relatively elaborate functional groups, which are not necessary for the actual function of the sensor principle, on the molecules applied in each case. A simplification of the preparability of such thin fluorescent layers with comparatively simple molecules is accordingly a crucial problem to be solved.

This problem is solved in the present invention by adsorbing polyionic macromolecules to which a fluorescent dye is bonded onto charged support materials by purely ionic interactions. The technique of generating layers with polyions is described in U.S. Pat. No. 5,208,111, issued on May 4, 1993, incorporated herein by reference. It has been found, surprisingly, that it is possible with this method to achieve higher fluorescent intensities than with Langmuir-Blodgett layers of comparable thickness and number, while the preparation, especially concerning apparatus, is considerably less elaborate.

SUMMARY OF THE INVENTION

The invention relates to an optical solid-phase biosensor which can be labelled with a dye $F_1$ and with a receptor molecule for the detection of analyte molecules in liquid phase, which can be labelled with a dye $F_2$ utilising the Förster energy transfer between $F_1$ and $F_2$, which consists of a) an optionally transparent support, b) a mono- or multilayer located thereon, c) contains chemically bonded in the uppermost layer or one of the uppermost layers the fluorescent dye $F_1$ as donor dye and d) an antibody or antigen as receptor covalently or ionically bonded to the uppermost layer, to which an e) antigen or antibody can be bound as analyte molecule which is in turn labelled with the fluorescent dye $F_2$, where the spacing between the dye molecules permits a radiationless Förster energy transfer, characterised in that one or more alternating layers of polyanions or polycations are employed as mono- or multilayer b), and in that the concentration of the bound analyte molecule is measured as a function of the increase in the relative fluorescence intensity of $F_2$ or the decrease in the fluorescence intensity of $F_1$ or the change in the ratio of the two intensities.

DETAILED DESCRIPTION OF THE INVENTION

Figure 1:
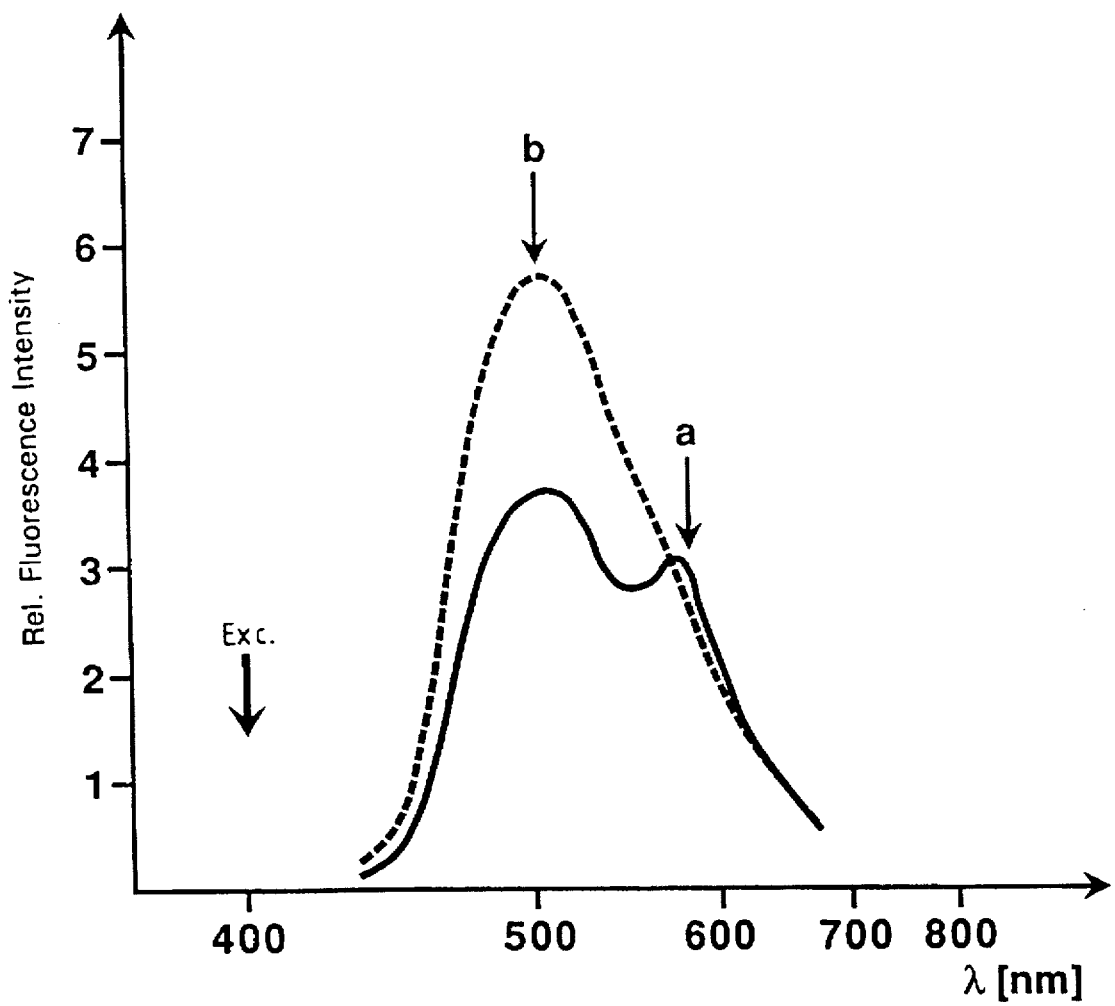
FIG. 1 depicts the relative fluorescence intensity versus wavelength for the measurement of the binding of TRITC-labelled anti-digoxin IgG via fluorescence (curve a) versus a no binding control (curve b).

Examples of suitable supports for the layers to be applied are glasses such as float glass or quartz glass, semiconductor materials such as silicon, plastics such as polyesters, vinyl polymers or polycarbonate, and metals. In order to be able to adsorb thereon a compound via ionic interactions, the support surface must have a sufficient number of charge carriers. With some of the materials mentioned, such as the glasses or surface-oxidised silicon, this is already the case to a certain extent. If this is insufficient, the support materials can also be loaded with ionic groups by chemical surface modification, for example with aminopropyl-ethoxy-dimethylsilane, as described in U.S. Pat. No. 5,208,111; issued on May 4, 1993; incorporated herein by reference. Oxidative treatment, for example by wet chemical oxidation, by corona discharge or by plasma treatment of the support materials, is also a suitable method known to the person skilled in the art for generating ionisable surfaces. As an alternative to this, the surfaces can also contain groups which are able to react chemically with the first layer which is to be applied, with the formation of covalent bonds, such as, for example, vinylidene chloride activation for loading with polyamino compounds.

Polyanions and polycations are required as adsorbing polyions. Suitable and preferred polycations are compounds with amino groups, such as polylysine, polyallylamine, polyvinylpyridine, dextrans modified with amino groups (for example DEAE-dextran), and chitosan. The amino compounds can be converted to the ionised state either by simple protonation or by quaternisation. To a small extent the amino groups can also be provided with functional groups such as, for example, the donor dye and/or reactive groups for attaching receptor molecules.

Suitable and preferred polyanions are polycarboxylic acids and polysulphonic acids. Examples of these are polyglutamate, polystyrenesulphonic acid, or dextran sulphate. It is also possible in this case, as in the case of the polycations, to attach functional groups. In the particular case of polystyrenesulphonic acid and other vinylic sulphonic acids it proves suitable to incorporate acrylated coumarin dyes or aminofluorescein. Examples of compounds of this type are described in Use Example 1 and in German Patent Application File No. P 41 14 482.1.

The construction of a functional multilayer now takes place by successive alternating immersion of the support in aqueous solutions which may also contain additions of organic solvents, of polyions, for example polycation, polyanion, polycation, and so on, with rinsing processes carried out in between. The polyions are preferably dissolved in concentrations between 0.01 and 1 g/l in the solvent, the optimum concentration depending on the molecular weight and the nature of the coating technique used and needing to be optimised in the individual case. The pH of the solution is adjusted to 10 or less, it being important that the polyamino compounds, unless they are already quaternised, are in protonated form and are not deprotonated and detached on subsequent immersion of the support in a polycation solution either. One of the uppermost layers (within the Förster radius of 5 to 10 nm) should contain that polyion to which a fluorescent dye is bonded. Then an antibody molecule or an antigen with reactive anchor group is, for example, immobilised on the uppermost layer. Suitable for the immobilisation of antibodies are the methods and reagents known from the literature, such as, for example, N-hydroxysuccinimide esters, isocyanates and isothiocyanates. Use Example 2 shows, as an alternative to this, the attachment of activated digitoxigenin to polylysine.

Examples of suitable donor/acceptor pairs for the Förster energy transfer are the following combinations of dyes:

| Donor (F₁) | Acceptor (F₂) |
| --- | --- |
| Fluorescein derivatives | Tetramethylrhodamine |
| Fluorescein derivatives | Texas red |
| Coumarin of the formula I | Tetramethylrhodamine |
| Coumarin of the formula II | Tetramethylrhodamine |

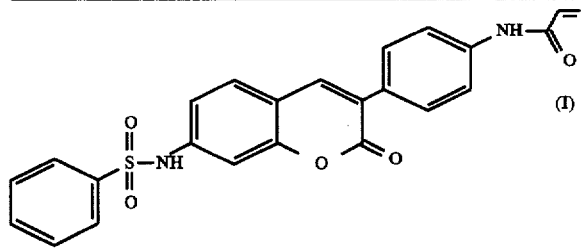

(I)

-continued

| Donor (F₁) | Acceptor (F₂) |
| --- | --- |

(II)

the coumarin dyes of formulae (I) and (II) can be prepared from the disclosure of U.S. Pat. No. 5,300,656, issued Apr. 5, 1994.

The acceptor dyes mentioned can be reacted in a manner known to the person skilled in the art, both with protein receptors and with various low molecular weight substances as long as they have amino groups. It is subsequently possible to detect at these binding sites, using a fluorescent dye complementary to that bonded in the film layers, a fluorescence-labelled binding partner by Förster energy transfer. For example, it is possible to bond to digitoxigenin-modified polylysine (Use Example 2) a monoclonal antibody, or a Fab fragment thereof, labelled with tetramethylrhodamine isothiocyanate (TRITC). In this system, free digoxin can be detected by displacement of the antibody from the solid phase or by previous reaction with the labelled antibody [analogous to: R. G. Sommer et al., Clin. Chem. 36, 201–206 (1990)].

Analytes are detected by simply contacting the coated support with the sample solution and subsequently measuring the fluorescence. A Förster energy transfer can be measured in conventional fluorescence spectrometers but also in apparatus specifically designed therefor, as described, for example, in the German Application with the File No. P 41 16 116.5.

USE EXAMPLES

1. Synthesis of coumarin-containing anionic polymers

The following substances are dissolved in 25 ml of dimethyl sulphoxide:

| Polymer | A [g] | B [g] | C [g] |
| --- | --- | --- | --- |
| Sodium p-styryl-sulphonate | 2 | 3 | — |
| Potassium sulphopropyl methacrylate | — | — | 2.66 |
| Coumarin I | 2 | 1 | — |
| Coumarin II | — | — | 1.33 |
| Azobisiso-butyronitrile | 0.02 | 0.02 | 0.02 |

Coumarin I =

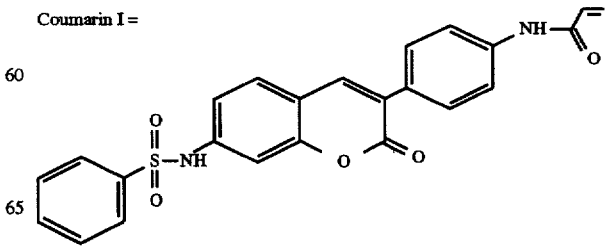

| Polymer | A [g] | B [g] | C [g] |
|---|---|---|---|

Coumatin II =

(structure of coumarin II derivative with Et₂N group, phenyl ring, NH-acetyl group, and lactone)

The solution is placed in the polymerisation apparatus.

The apparatus is evacuated and charged with extra pure nitrogen, and this process is repeated three times; the solution is subsequently heated to 65° C. and reacted for 15 h. The reaction solution is added dropwise to 200 ml of acetone, and the resulting precipitate is filtered off and dried. The crude polymer is subjected to an ultrafiltration (cutoff 10,000 dalton).

Yield 70–80% of theory.

Physical data of the polymers prepared:

Fluorescence (measured in HaO, pH 10)

|  | Polymers A, B: | Polymer C |
|---|---|---|
| $\lambda_{exc}$ | 385 nm | 410 nm |
| $\lambda_{em}$ | 498 nm | 499 nm |

Molecular weights ($\overline{M}_n$, measured by aqueous gel permeation chromatography):

| Polymer A | Polymer B | Polymer C |
|---|---|---|
| 150 000 | 250 000 | 180 000 |

2. Derivatisation of polylysine with digitoxigenin 25 mg of poly-DL-lysine are dissolved in 15 ml of methanol, and 20 µl of triethylamine are added. While stirring at room temperature, 22 mg of digitoxigenin-(6-aminocaproyl-carboxy)-N-hydroxysuccinimide in 5 ml of isopropanol/chloroform (1:1, v/v) are added dropwise. The solution is subsequently stirred under reflux for 2 h and then at room temperature for 8 h. The reaction mixture is evaporated in vacuo, taken up in 2 ml of water and chromatographed on a Sephadex G-25 column (50 cm×16 cm diameter, UV detection 254 nm, mobile phase: water). The product-containing fractions are freeze-dried.

Yield: 27 mg (60% of theory)

²H-NMR (250 MHz, CDCl₃): 1.45 (m), 1.71 (m), 2.66 (s), 2.99 (m), 4.30 (m), 4.80 (m) ppm.

An immunological determination of the digitoxigenin incorporation (Miles Seralyzer Digoxin Assay Kit) showed a content of digoxin equivalents of 2.5% by weight.

3. Cleaning and pretreatment of a glass plate 3.1. Basic cleaning

A slide made of float glass is treated with water in an ultrasonic bath for 1 minute and carefully dried with nitrogen, cleaning the surfaces free of dust. The plate is then placed for preliminary cleaning in a mixture of concentrated sulphuric acid and hydrogen peroxide (7:3, v/v) and treated therein at 80° C. in the ultrasonic bath for one hour. After cooling to room temperature, the plate is treated in water in the ultrasonic bath 3 times for 60 seconds each time and washed free of acid with water. It is subsequently placed in a mixture of H₂O/H₂O₂/NH₃ (5:1:1, v/v/v) and treated therein at 80° C. for 5 minutes. The plate is then carefully washed with water until free of salts.

3.2. Aminosilanisation

Before the silanisation reaction, the plate is treated in methanol, methanol/toluene (1:1, v/v) and toluene for 2 minutes each to remove traces of water. It is then left to react in a 5% strength (v/v) 3-aminopropyldimethylethoxysilane solution in toluene under a nitrogen atmosphere for 15 h. Finally, the plate is treated in an ultrasonic bath with toluene, toluene/dimethyl sulphoxide (DMSO) (1:1, v/v) and DMSO for 1 minute each.

4. Preparation of a film element with monomolecular fluorophore-containing film

General coating method

A) A sample plate is immersed in solution A (polycation) for 20 minutes and then immersed in 10 ml portions of water 3 times for 20 seconds each and left to dry.

B) It is subsequently immersed in solution B (polyanion) for 20 minutes and again in 10 ml portions of water 3 times for 20 seconds, and left to dry.

4.

1. On float glass, no loading with amino groups

The slides made of float glass are pretreated as in Example 3.1. and loaded by the above procedure by successive immersion in the following solutions:

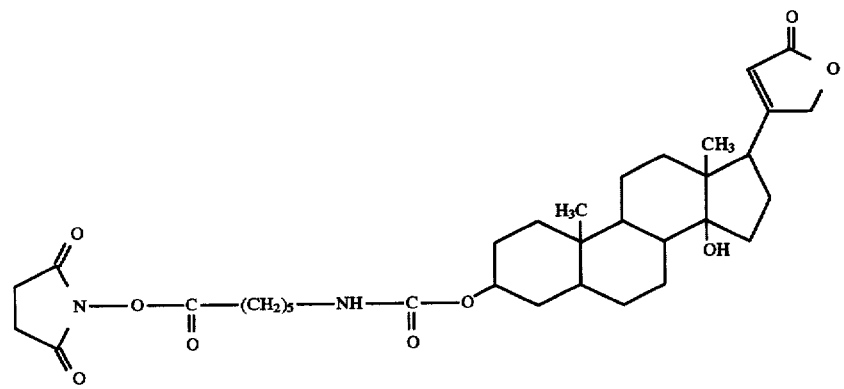

4.1.1.

Solution A: 5 mg of polylysine in 10 ml of 0.05M carbonate buffer pH 8;

Solution B: 5 mg of polymer C in 10 ml of 0.05M carbonate buffer pH 8.

4.1.2.

Solution A: 0.5 mg of DEAE-dextran in 10 ml of 0.05M carbonate buffer pH 8;

Solution B: 0.5 mg of polymer C in 10 ml of 0.05M carbonate buffer pH 8.

4.1.3.

Solution A: 10 mg of polylysine in 10 ml of 0.05M carbonate buffer pH 8;

Solution B: 1 mg of polymer C in 10 ml of 0.05M carbonate buffer pH 8.

4.1.4.

Solution A: 1 mg of DEAE-dextran in 10 ml of 3 mM hydrochloric acid;

Solution B: 1 mg of polymer C in 10 ml of 3 mM hydrochloric acid.

4.1.5.

Solution A: 0.1 mg of polyvinylpyridine (Reilline 2200) in 10 ml of 3 mM hydrochloric acid;

Solution B: 10 mg of polymer A in 10 ml of 3 mM hydrochloric acid.

4.2. On float glass, loaded with amino groups

The slides made of float glass are pretreated as in Example 3.2. and, in a modification of the general procedure, loaded merely by immersion in solution B. The solutions from 4.1.1. to 4.1.4. can be used.

4.3. On polyester film

A piece of polyester film surface-activated with vinylidene chloride is coated, without further cleaning steps, in analogy to the above general procedure. The solutions from 4.1.1. to 4.1.4. can be used.

5. Measurement of the binding of TRITC-labelled anti-digoxin IgG to the layer element A support coated as in Example 4.1.3. is, subsequent thereto, coated with a specifically binding layer by immersion in a solution of 0.1 mg/ml digitoxigenin-derivatised polylysine (Example 2) and washing according to the general procedure.

The plate is subsequently wetted with 50 µl of a solution of TRITC-anti-digoxin IgG (prepared by reacting tetramethylrhodamine isothiocyanate and anti-digoxin IgG; protein concentration 0.1 mg/ml). After rinsing with a buffer (15 mM $KH_2PO_4$, 25 mM citrate, 1 mM $MgCl_2$, 50 mM KCl, 0.4 g/l $NaN_3$, 1 g/l bovine serum albumin, pH 6.4) the fluorescence is measured once again, that of the coumarin from polymer C (509 nm) being quenched in favour of the fluorescence of TRITC (587 nm) (FIG. 1, curve a). As a control, underivatised polylysine is employed in place of the digitoxigenin-derivatised polylysine, in the same concentration, which makes the uppermost layer incapable of binding, and no energy transfer takes place (FIG. 1, curve b).

What is claimed is:

1. An optical solid-phase biosensor which is labelled with a dye $F_1$ and with a receptor molecule for the detection of analyte molecules in liquid phase, which is labelled with a dye $F_2$ utilising the Förster energy transfer between $F_1$ and $F_2$, which consists of
   a) an optionally optically transparent support,
   b) a multilayer located thereon, made from polymers containing ionically charged groups, where each layer contains ions of the same charge, said ions of the first layer having the opposite charge of the optionally modified support and, in case of further layers, each further layer having a charge opposite that of the previous layer,
   c) wherein said multilayer forming polymers, in addition to the charged groups, contain covalently bonded in the uppermost layer or one of the uppermost layers the fluorescent dye $F_1$ as doner dye and
   d) an antibody or antigen as receptor covalently or ionically bonded to the uppermost layer, to which
   e) an antigen or antibody is bound as analyte molecule which is in turn labelled with the fluorescent dye $F_2$, where the spacing between the dye molecules permits a radiationless Förster energy transfer, wherein at least one layer of polyanions and at least one layer of polycations are used and wherein, when more than one of each are used, the polyanion layers and polycation layers alternate with respect to each other, one after the other, and wherein the concentration of the bound analyte molecule is measured as a function of the increase in the fluorescence intensity $F_1$ or the decrease in the fluorescence intensity $F_2$ or the change in the ratio of the two intensities.

2. The optical biosensor of claim 1, in which float glass, quartz glass, silicon, polyesters, vinyl polymers or polycarbonate is employed as support material a).

3. The optical biosensor of claim 1, in which the polyanionic compound is polyglutamic acid, polystyrenesulphonic acid, dextran sulphate or a copolymer of styrenesulphonic acid or other vinylic sulphonic acid and of a vinyl derivative of a fluorescent dye.

4. The optical biosensor of claim 3, in which the polyanionic compound is a copolymer of styrenesulphonate or sulphopropyl methacrylate and the acrylate of a coumarin dye.

5. The optical biosensor of claim 1, in which the polycationic compound is polylysine, polyallylamine, polyvinylpyridine, chitosan or the ammonium salt thereof quaternized by permethylation, or DEAE-dextran.

6. The optical biosensor of claim 5, in which the polycationic compound is a polyamino compound, such as polylysine or polyallylamine, partially derivatised with fluorescein isothiocyanate or another reactive dye.

7. The optical biosensor of claim 1, wherein the pair of dyes $F_1$ and $F_2$ which are suitable for Förster transfer and which are employed are fluorescein derivatives and tetramethylrhodamine, fluorescein derivatives and Texas red, coumarin of the formula I and tetramethylrhodamine

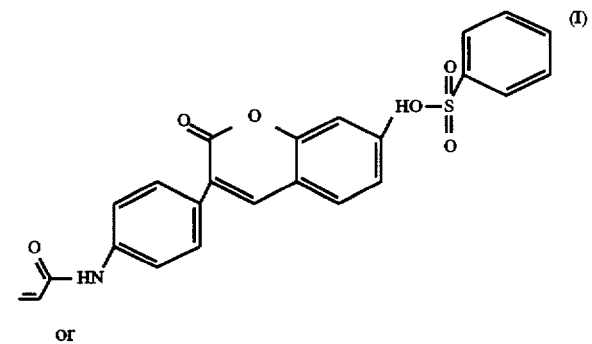

or coumarin of the formula II and tetramethylrhodamine

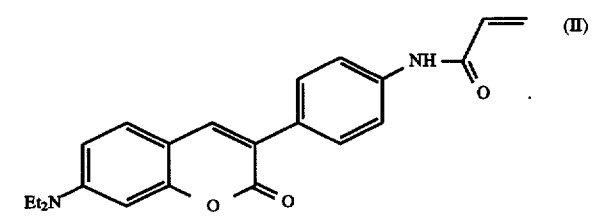

8. The optical biosensor of claim 7, in which coumarin of the formula I and tetramethylrhodamine or coumarin of the formula II and tetramethylrhodamine is employed as the pair of dyes $F_1$ and $F_2$.

* * * * *

UNITED STATES PATENT AND TRADEMARK OFFICE
CERTIFICATE OF CORRECTION

PATENT NO.  : 5,711,915
DATED       : January 27, 1998
INVENTOR(S) : Siegmund, et al.

It is certified that error appears in the above-identified patent and that said Letters Patent is hereby corrected as shown below:

Col. 8, line 10   Delete " $F_1$ " and substitute -- $F_2$ --

Col. 8, line 11   Delete : $F_2$ " and substitute -- $F_1$ --

Col. 8, line 43   Delete " 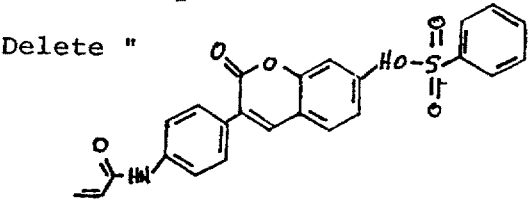 "

and substitute -- 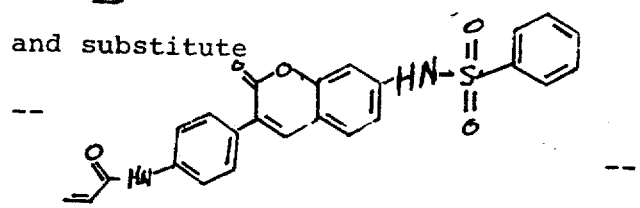 --

Signed and Sealed this

First Day of December, 1998

Attest:

BRUCE LEHMAN

Attesting Officer    Commissioner of Patents and Trademarks